United States Patent [19]

Goldberg

[11] 4,187,290

[45] Feb. 5, 1980

[54] CARRIER AND DISPERSAL MECHANISM FOR A MICROORGANIC LARVICIDE

[75] Inventor: Leonard J. Goldberg, Albany, Calif.

[73] Assignee: The United States of America as represented by the Secretary of the Navy, Washington, D.C.

[21] Appl. No.: 30,961

[22] Filed: Apr. 18, 1979

Related U.S. Application Data

[62] Division of Ser. No. 888,083, Mar. 20, 1978.

[51] Int. Cl.$^2$ .......... A01N 15/00

[52] U.S. Cl. .......... 424/93

[58] Field of Search .......... 424/93

[56] References Cited

U.S. PATENT DOCUMENTS

| | | | |
|---|---|---|---|
| 3,113,066 | 12/1963 | Emond | 424/93 |
| 3,271,243 | 9/1966 | Cords et al. | 424/93 |
| 3,415,744 | 12/1968 | Buetow | 210/22 |
| 3,415,746 | 12/1968 | Buetow | 210/59 |
| 3,420,933 | 1/1969 | Cords et al. | 424/93 X |
| 3,651,215 | 3/1972 | Ibvkl et al. | 424/93 |

FOREIGN PATENT DOCUMENTS

| | | | |
|---|---|---|---|
| 2250604 | 4/1963 | Fed. Rep. of Germany . | |
| 1284150 | 11/1968 | Fed. Rep. of Germany | 424/93 |
| 1577690 | 8/1969 | France . | |
| 481281 | 8/1975 | U.S.S.R. | 424/93 |

OTHER PUBLICATIONS

Goldberg et al., Mosquito News (37)3: 465–470, Sep. 1977,Effectiveness of *Bacillus sphaericus* var. *fusiformis* (SS11-1) As A Potential Mosquito Larval Control Agent: The Role of Variations In Natural Microbial Flora In the Larval Environment.

Goldberg et al., Mosquito News 37(3): 355–358, Sep. 1977, A Bacterial Spore Demonstrating Rapid Larvicidal Activity Against *Anopheles sergentii, Uranothenia unguiculata, Culex univitattus, Aedes aegypti* and *Culex pipiens* (Biological Control).

Goldberg et al., Proc. Pap. Annu. Conf. Calif. Mosq. Control Assoc. V 42: 169–174 (1974), Mortality of *Culex tarsaus* Mosquito Larvae Obtained in Laboratory Studies Using Various Combinations of *Bacillus thuringensis* (HD—1) With Two Growth Regulators.

Nishiuchi, Y., Suisan Zohoku, 1975, 23(3): 125–128, Toxicity of Formulated Pesticides to Some Fresh Water Organisms.

Dawson et al., J. Hazard, Mater. 1977, 1(4): 303–318, The Acute Toxicity of 47 Industrial Chemicals to Fresh and Salt Water Fishes.

*Primary Examiner*—Shep K. Rose

*Attorney, Agent, or Firm*—R. S. Sciascia; Charles D. B. Curry

[57] ABSTRACT

A method of controlling mosquito larvae, by using a spore-forming bacillus ONR-60A obtained from screening clonal isolates from soil samples of known mosquito larval breeding sites. A larvicide comprising the bacillus and a carrier is formulated as a buoyant colloidal suspension which stabilizes just under the surface of the water to concentrate in the feeding zone of many varieties of mosquito larvae.

6 Claims, No Drawings

CARRIER AND DISPERSAL MECHANISM FOR A MICROORGANIC LARVICIDE

This application is a division of patent application Ser. No. 888,083 filed Mar. 20, 1978, by Leonard J. Goldberg.

BACKGROUND OF THE INVENTION

1. Field of the Invention

This invention relates to a method of mosquito larval control. More specifically, the invention relates to larval control by use of a novel spore-forming bacillus and a unique carrier for dispersal of the bacillus. In particular, the invention relates to a unique strain of spore-forming bacillus belonging to the species *Bacillus thuringiensis* and a unique buoyant colloidal suspension by which the bacillus is carried and dispersed into known habitats of mosquito larvae.

2. Description of the Prior Art

Two major approaches have evolved in the development of effective agents for larval control. One approach is the use of chemical compounds of varying toxicity. The other approach is the development and use of biological microorganisms with high larvicidal activity.

The major shortcoming of the first approach is that new compounds of increased toxicity must be developed or dosage levels of standard compounds increased to counter elevated, adaptive resistance by insect populations to standard insecticides. An unfortunate byproduct of this approach to date is increased toxicity to other lifeforms within the region of application.

Biological microorganisms to date demonstrate a lower or negligible development of resistance in host vectors. Such biological microorganisms may be developed offering improved lethality against host vectors, improved specificity against particular host vectors, and better methods of application without correspondingly lethal effects upon other lifeforms within the region of application.

Technology in the development of bacterial entomotoxins to control mosquito larvae is well known. Some of the entomotoxins employed have been *Bacillus sphaericus Neide, Bacillus sphaericus* var fusiformis, and a bicrystalliferous strain of *Bacillus thuringiensis.* In particular, selected strains of *Bacillus thuringiensis* have been used in Europe and America as major components of microbial insecticides having a toxic effect on general agricultural and forest insect pests. (A. Krieg: *Bacillus thuringiensis,* Berliner, Berlin, 1961.) To date, however, use of *Bacillus thuringiensis* against insects directly harmful to humans without concomitant adverse effects has not been employed. The present invention is in part a unique strain of *Bacillus thuringiensis,* hereinafter referred to as ONR-60A, having high, long-lasting, selectively toxic effects on mosquito larvae with no apparent adverse effects on other lifeforms.

Information gathered from all the above studies indicates that several requirements must be met by any microbial entomotoxin before it can be safely and practically used in the field. These requirements are: (1) effective larval control, e.g., effective dosage levels having 95% lethality when employed ($ED_{95}$), should require less than $10^6$ cells/cm$^2$ of larval pond surface area; (2) the toxin should be formulated as a buoyant colloidal suspension such that a toxic concentration will stabilize just below the surface of the larval habitat; (3) larvicidal activity should be retained under conditions of heat and exposure to ultraviolet radiation; and (4) the environmental impact following the use of a selected entomotoxic formulation must not be damaging to a desired ecological balance or otherwise adversely affect other lifeforms within the zone of entomotoxin application.

Regarding criteria (2) listed above, the natural breeding habitat of mosquito larvae is in ponds, lakes, streams, marshes and the like in the shallow littoral zone. Most mosquito larvae must surface for oxygen and as a consequence feed in the region just below the water's surface. Larvicides employed as oil films asphyxiate the larvae as they surface to breath but have the disadvantage that the oil slick is deletorious to much other flora and fauna as well. Further, field studies indicate larvae avoid areas having such oil slicks.

Dust layer and oil film insecticides designed to float on the surface of the water are strongly affected by wind currents, water currents and the like and have serious problems in application and maintenance. Typical of such problems is the drifting and accumulation of such larvicides upon land areas during application or the formation of scum layers on the surface of the water that subsequently concentrate upon land areas.

Larvicidal formulations having non-buoyant characteristics are disadvantageous in that they are largely ineffective if dispersed in water having greater depth than the feeding zone of the larvae. Effectiveness is reduced even more where the non-buoyant formulation is a contact insecticide.

When microbial entomotoxins are employed, the specificity or range of the toxic effect of the particular microorganism is extremely important since it is this characteristic that principally determines its utility and the extent of its use. For example, within the species *Bacillus cereus,* some variant strains have pathogenic effects limited to a narrow range of insects while other strains have no observed toxic effects at all even though they have essentially identical morphological characteristics. (Ibuki, et al U.S. Pat. No. 3,651,215). As mentioned supra, *Bacillus thuringiensis* another species of microorganism having great variation of effects by strains within the species, has had little use to date as an entomotoxin against insects directly harmful to humans. Although some strains have been isolated that are effective against mosquito larvae, they have too narrow a range to be of great utility.

Table I illustrates the wide variation of larvicidal activity, or non-activity, of many strains of *Bacillus thuringiensis* and clearly points out that larvicidal activity is not associated with any single serotype and that the only real characterization or measure of utility and novelty of a microbial entomotoxin is its larvicidal activity. Persons skilled in the art of working with such entomotoxins can routinely cause trivial mutations of a particular entomotoxic agent having no significantly different larvicidal activity, but having some morphological characteristics changed by the trivial mutation. The present invention contemplates such trivial mutations.

TABLE I

Summary of screening of test culture of *Bacillus thuringiensis* (BAO68) for larvicidal activity against *Culex tarsalis* (K.L.) 1st instar test larvae.

| Isolates Demonstrating Larvicidal Activity |
| --- |

TABLE I-continued

Summary of screening of test culture of *Bacillus thuringiensis* (BAO68) for larvicidal activity against *Culex tarsalis* (K.L.) 1st instar test larvae.

| Original Designation | Serotype | Code Number |
|---|---|---|
| kurstaki | H3a,3b* | (2536-9693TW) |
| kurstaki | " | (2819-9763F) |
| aizawai | H7* | (1850-9762C) |
| tolworthi | H9* | (NPI-460) |
| sotto | H4a,4b | (NPI-180-5-2) |
| thuringiensis | H1 | (NPI-186-104) |
| thuringiensis | " | (NPI-185-104) |
| thuringiensis | " | (NPI-201-113) |
| thuringiensis | " | (NPI-197-105) |
| thuringiensis | " | (NPI-198-105) |
| thuringiensis | " | (NPI-199-105) |
| sotto | H4a,4b | (NPI-194-101) |

Isolates Demonstrating No Larvicidal Activity

| Original | Serotype | Code Number |
|---|---|---|
| kurstaki | H3a,3b* | (720619A) |
| B. thuringiensis var.? | H5a,5b | (730130-1) |
| thuringiensis | H1* | (1840-182C) |
| finitimus | H2* | (NPI-451) |
| subtoxious | H6* | (NPI-456) |
| entomocidus | H6* | (NPI-457) |
| aizawai | H7* | (NPI-458) |
| morrisoni | H8* | (NPI-459) |
| darmastadiensis | H10* | (NPI-461) |

*Cultures marked with an asterisk have had recent confirmation. The remainder are based on information available before 1963, and therefore, there is a possibility those classifications are not accurate.

SUMMARY OF THE INVENTION

The present invention may be briefly summarized as a method of controlling mosquito larvae by using a spore-forming bacillus ONR-60A obtained from screening clonal isolates from soil samples of known mosquito larval breeding sites. The larvicide comprising the bacillus and a carrier is formulated as a buoyant colloidal suspension which stabilizes just under the surface of the water to concentrate in the feeding zone of mosquito larvae.

A primary object of the present invention is the development of a unique microbial entomotoxin and a carrier having high, long-lasting and very selective toxic effect on mosquito and mosquito-like larvae without adversely affecting the environment within the zone of application.

DESCRIPTION OF THE PREFERRED EMBODIMENT

The present inventor, having studied mosquito breeding habitats in Israel discovered unique null zones of mosquito larvae activity within regions of normally high mosquito and mosquito larvae activity, analyzed a number of soil samples from the null zones to determine the cause of such unusually high larvicidal activity. The present inventor devised an empirical method for locating and isolating microorganisms having unique, high larvicidal activity and in the instant case succeeded in isolating the microorganism herein referred to as ONR-60A. He further devised a unique carrier for dispersal of the new larvicide.

A sample of the microorganism has been deposited with the International Culture Depository, Columbus, Ohio, 43210. In subsequent screening and analysis by WHO, it has been identified as a unique strain of *Bacillus thuringiensis* and has been granted an accession number within this depository as WHO/CCBC 1897.

The spores of ONR-60A were successfully isolated and a pure biological strain obtained in the following way. Known mosquito larvae habitats were searched and both moist and dry soil samples were taken from null zones within the habitat wherein larvicidal activity within the soil was uncommonly high and the larvae population uncommonly low. A liquid dilution was then experimentally determined to provide easily separable clonal isolation of the microorganisms contained in the samples. In the instant case, 30–100 clones/agar plate was chosen as a manageable number. The plates were then inoculated to obtain a sufficient number of well-separated and distinctive clonal isolates. Inoculated plates were incubated for 48 hours at 30° C. and then held at room temperature, 22°–26° C., for approximately 48 additional hours to obtain a visually evident, clearly-defined clonal morphology. Several examples of each clonal isolate were then selected from each test soil sample for screening. A manageable number of such cloned isolates were screened in the ensuing larval test runs. In the instant case, the number of isolates screened per larval test run was approximately 100–150.

Screening for each clone was accomplished by using a row of five wells, each well having 4 ml of sterile liquid and containing two or three test larvae. Each row was then challenged using one drop/well, 0.04 ml/well, of a nominal $10^9$ cells/ml test slurry obtained by scrubbing the agar surface growth with a dally rod and 5 ml of a sterile diluent. The test slurry obtained was approximately $10^9$ cells/ml, thus resulting in an initial larval screening challenge of approximately $10^7$ cells/ml. Any clone which demonstrated over 80% mortality in 24–48 hours was considered for further quantitative analysis.

Clonal isolates selected for additional screening were inoculated onto both a nutrient agar and a test agar and incubated as required to get a visually-evident, clearly-defined clonal morphology on each agar surface. The agar surface growths were removed by scrubbing each with a dally rod and 5 ml of a sterile diluent. One or two trays of first to second instar *C. pipiens* complex larvae, for example, were then used in a ½ test challenge dilution series of each of the growths on each agar surface with 15–30 larvae/test dilution. Each tray contained 25 wells with three larvae/well. The clonal isolate ONR-60A, observed to demonstrate larvicidal activity independent of the agar surface on which it was grown, was then produced in quantities for field test purposes by methods familiar to those in the art.

Tables II and III illustrate the toxicity of ONR-60A against various mosquito larvae species. Unlike prior strains of *Bacillus thuringiensis* having too narrow a range of toxic effect, as mentioned supra, ONR-60A possesses utility in application against a broad range of mosquito larvae species.

TABLE II

Relative Toxicity, estimated $ED_{50}$, of ONR-60A Against Different Species of Mosquito Larvae

| Species | Concentration (cells/ml) |
|---|---|
| Anopheles sergentii | $5 \cdot 10^5$ |
| Anopheles superpictus | $2 \cdot 10^5$ |
| Anopheles hyrcanus complex | $2 \cdot 10^5$+ |
| Anopheles stephensi | $2 \cdot 10^5$ |
| Uranotaenia unguiculata | $3 \cdot 10^4$ |
| Culex univittatus | $2 \cdot 10^4$ |
| Aedes aegypti | $1 \cdot 10^4$ |
| Culex pusillus | $7 \cdot 10^3$ |
| Culex pipiens (m) | $6 \cdot 10^3$ |
| Culex pipiens complex | $5 \cdot 10^3$ |

TABLE II-continued

| Relative Toxicity, estimated $ED_{50}$, of ONR-60A Against Different Species of Mosquito Larvae | |
|---|---|
| Species | Concentration (cells/ml) |
| Culex theileri | 3 * $10^3$+ |
| Culex torrentium | 3 * $10^3$+ |
| Culisetta sp. | 3 * $10^3$ |
| Culex (Neoculex) deserticola | 2 * $10^3$ |
| Culex tritaeniorhychus | 4 * $10^2$+ |

+Concentration as a function of habitat was tested, this was the strongest concentration employed for any habitat.

TABLE III

Toxicity of ONR 60A Against Selected Species of Mosquito Larvae Showing % Mortality

| Species/Stage | Concentration (cells/ml) | Time Period | % Mortality |
|---|---|---|---|
| *Aedes sierrensis* | $10^4$ | 144 hours | 45.5 |
| First instar | $10^5$ | 144 hours | 92.2 |
| | $10^6$ | 144 hours | 100.0 |
| *Aedes sierrensis* | $10^4$ | 140 hours | 11.6 |
| Third instar | $10^5$ | 140 hours | 95.0 |
| | $10^6$ | 17 hours | 100.0 |
| *Culiseta incidens* | $10^4$ | 17.5 hours | 0 |
| Second instar | $10^5$ | 17.5 hours | 100.0 |
| | $10^6$ | 17.5 hours | 100.0 |
| *Culiseta incidens* | $10^4$ | 17.5 hours | 0 |
| Third instar | $10^5$ | 17.5 hours | 100.0 |
| | $10^6$ | 17.5 hours | 100.0 |
| *Culiseta incidens* | $10^4$ | 17.5 hours | 0 |
| Fourth instar | $10^5$ | 17.5 hours | 78.9 |
| | $10^6$ | 17.5 hours | 100.0 |

Table IV illustrates the toxic effects of ONR-60A against selected non-target organisms. Note that only the genus Dixa, closely related to mosquitoes was affected. The planktonic crustaceans tested showed no mortality due to the entomotoxin. As these groups of animals are the base of the food pyramid in most aquatic ecosystems, the lack of adverse effects is quite important. Further, in agricultural screening tests devised from criteria established by the EPA, ONR-60A showed no useful larvicidal activity against the target agricultural insects, thus clearly indicating a totally unique strain of *Bacillus thuringiensis.* Still further, ONR-60A demonstrated no significant loss in larvicidal activity following heat shock for 20 minutes at 60° C. or following exposure to ultraviolet radiation (2537A°) sufficient to reduce the viable spore count to less than 0.1% of its initial value. Hence, toxic activity can be attributed to an ultraviolet and heat-stable endotoxin.

TABLE IV

Toxicity of ONR-60A Against Selected Non-Target Organisms

| Species | Concentration (cells/ml) | Time Period | % Mortality |
|---|---|---|---|
| *Hyallela azteca* | $10^5$ | 10 days | 0 |
| | $10^6$ | 10 days | 0 |
| *Simocephalus vetulus* | $10^5$ | 10 days | 2 |
| | $10^6$ | 10 days | 3 |
| *Macrocyclops, sp.* | $10^5$ | 5 days | 0 |
| | $10^6$ | 5 days | 0 |
| *Dugesia dorotocephala* | $10^5$ | 10 days | 0 |
| | $10^6$ | 10 days | 0 |
| *Hyla regilla* | $10^5$ | 10 days | 0 |
| | $10^6$ | 10 days | 0 |
| *Alotanypus venusta* | $10^5$ | 8 days | 0 |
| | $10^6$ | 8 days | 60 |
| *Dixa, sp.* | $10^5$ | 17.5 hours | — |
| | $10^6$ | 17.5 hours | 100 |
| *Gambusia affinus holbrooki* | $10^7$ | 14 days | 0 |
| *Gyrinidae* | $10^7$ | 14 days | 0 |
| *Cladocerans* | $10^7$ | 7 days | 0 |
| *Amphipoda* | $10^7$ | 4 days | 0 |
| *Dytiscidae* | $10^6$ | 4 days | 0 |
| *Notonecta glauca* | $10^6$ | 4 days | 0 |
| *Hemiptera* | $10^6$ | 4 days | 0 |
| *Corixidae* | $10^7$ | 3 days | 0 |
| *Planaria* | $10^7$ | 3 days | 0 |
| *Simuliidae* | $10^6$ | 3 days | 0 |
| *Tabanidae* | $10^7$ | 24 hours | 0 |
| *Ephemeroptera* | $10^7$ | 24 hours | 0 |

Table V illustrates comparative larvicidal activities of ONR-60A and *Bacillus sphaericus* (SSII-1), a current very important microbial entomotoxin. ONR-60A possesses considerably superior larvicidal activity over *B. sphaericus* (SSII-1), approximately a 30-fold increase for $ED_{50}$ against *Culex pipiens* (complex). It also shows similarly high activity against Anopheles sergentii.

TABLE V

Comparaive Dose Response of Microencapsulated Formulation of ONR-60A vs 36-Hr N2X Agar Test Culture of Bacillus Sphaericus (SSII-1) Against Anopheles Sergenti and Culex Pipiens (complex)

| Larvae Species | Concentration (Cells/ml) | | % Mortality |
|---|---|---|---|
| | Bacillus sphaericus | ONR-60A | |
| Culex pipiens (complex) | 3.5 * $10^5$ | 2.8 * $10^4$ | 25 |
| | 8.2 * $10^5$ | 3.6 * $10^4$ | 50 |
| | 1.8 * $10^6$ | 5.5 * $10^4$ | 75 |
| | 1 * $10^7$ | 2.0 * $10^5$ | 100. |
| Anopheles sergentii | No data | 3.1 * $10^5$ | *25 |
| | No data | 5.0 * $10^5$ | *50 |
| | No data | 8.0 * $10^5$ | *75 |
| | No data | 4.6 * $10^6$ | *90 *90 |

*Response time = 6 hours

It must be emphasized that in the screening of clonal isolates to obtain unique biological strains of spores possessing unusually high larvicidal activity, two classes of agar surfaces should be employed. One class should be the class of agars which elicit toxin production by current bacterial organisms such as *Bacillus sphaericus* (SSII-1). An example would be the agar in commercial use for such production, N2X. Use of such a test agar quickly eliminates from consideration all spores not demonstrating toxic activity when grown on an agar surface from this class as potentially of no commercial utility. The other class should be the class of nutrient agars which do not normally elicit toxin production by bacterial organisms normally found in the soil. The ability of spores to form entomotoxins when grown on such surfaces seems correlated with toxin stability, an extremely important toxin characteristic. In the instant invention, none of the other screened spores, including *Bacillus sphaericus* (SSII-1), demonstrated useful toxic activity when grown on the nutrient control agar surface. Only ONR-60A demonstrated toxic activity independent of the agar surface on which grown. Thus employment of the nutrient control agar aids in isolating unique strains having stable toxin.

The present larvicide is effectively applied not to the adult mosquitoes but to the larvae. As such, it is necessary in the present invention for the larvae to ingest the spores of ONR-60A. The carrier mechanism by which ONR-60A is dispersed will now be considered. The dried spores of ONR-60A are produced for dispersal with the carrier by conventional techniques familiar to those skilled in the art.

An oleaginous, non-mineral-derived liquid of choice is put into solution with dioxane. A number of dried spores of ONR-60A is then added to the solution to form a colloidal suspension having concentration suitable for the desired application. Addition of water to the suspension results in the dioxane diffusing in the water and the oleaginous liquid nucleating about and microencapsulating the cells of ONR-60A to form a buoyant, colloidal suspension wherein the particle density of the cell plus the nucleated liquid is less than one. The water may be added to the first suspension and the second suspension transported to the dispersal site or the first suspension may be injected into the water causing the second suspension to then formulate at the dispersal site.

The oleaginous liquid to be employed must be hydrophilic in nature. Although the combination of spore and nucleated liquid about the spore possesses positive buoyancy, the hydrophilic phenomena of the liquid interacting with the surface tension phenomena of the water causes the suspension to lie just below the surface of the water within the principle feeding zone of the mosquito larvae. Examples of, although by no means limited to, such liquids are corn oil, cottonseed oil and lanolin in combination with some conventional wetting agent well-known to those in the art. The liquid preferred for formulating the buoyant colloidal suspension is jojoba oil as field tests indicate the hydrophilic properties of the oil may result in requiring little or no additional wetting agent.

The buoyant character of this formulation of ONR-60A provides for the concentration of the toxic colloid in the primary feeding zone of mosquito larvae, i.e., in a liquid layer just below the surface. One liter of microencapsulated formulation of $10^{10}$ spores/ml of ONR-60A is projected to provide, for example, a lethal concentration to mosquito larvae over an area of 1000 $m^2$.

Obviously, as mentioned supra, trivial mutations of the instant microorganism and many modifications of the instant carrier means are possible in light of the above teachings. Such trivial mutations of the microorganism and such modifications of the carrier are contemplated and are within the scope of the appended claims.

What is claimed is:

1. A carrier for dispersing spores of a microbial entomotoxin employed as an oral bacterial larvicide comprising:

(a) dioxane;

(b) oleaginous liquid, said liquid being dissolved in said dioxane;

(c) microbial entomotoxin admixed with said solution of dioxane and said oleaginous liquid such that said oleaginous liquid nucleates about said spores upon introduction of water to admixture.

2. The formulation of claim 1 wherein said microbial entomotoxin is WHO/CCBC 1897.

3. The formulation of claim 1 wherein said oleaginous liquid has specific gravity less than 1.

4. The formulation of claim 1 wherein said oleaginous liquid is non-mineral derived.

5. The formulation of claim 1 wherein said oleaginous liquid is hydrophilic.

6. The formulation of claim 1 wherein said oleaginous liquid is jojoba oil derived from the jojoba plant.

* * * * *